United States Patent [19]

Brenholt

[11] 4,265,762
[45] May 5, 1981

[54] FILTER ASSEMBLY FOR USE IN THE FILTRATION OF MEDICAL TREATMENT LIQUIDS

[75] Inventor: David L. Brenholt, Dundas, Minn.

[73] Assignee: Donaldson Company, Inc., Minneapolis, Minn.

[21] Appl. No.: 963,441

[22] Filed: Nov. 24, 1978

[51] Int. Cl.³ ............................................. B01D 31/00
[52] U.S. Cl. ................................ 210/321.1; 210/436; 210/451; 210/455; 210/472; 210/477
[58] Field of Search .......... 422/48; 210/321 B, 321 R, 210/321 A, 455, 445, 446, 232, 436, 472, 483, 451, 477, 448; 55/158

[56] References Cited

U.S. PATENT DOCUMENTS

| | | | |
|---|---|---|---|
| 1,782,531 | 11/1930 | Fokker | 210/153 |
| 2,664,395 | 12/1953 | Marchand | 210/321 B |
| 2,687,997 | 8/1954 | Marchand | 210/321 A |
| 2,765,923 | 10/1956 | Novak | 210/499 |
| 3,034,505 | 5/1962 | Sobol | 210/321 B |
| 3,217,889 | 11/1965 | Berg | 210/448 |
| 3,399,040 | 8/1968 | Ilg | 210/321 R |
| 3,506,130 | 4/1970 | Shaye | 210/446 |
| 3,631,654 | 1/1972 | Riely et al. | 55/159 |
| 3,727,612 | 4/1973 | Sayers et al. | 210/22 |
| 3,905,905 | 9/1975 | O'Leary et al. | 210/436 |
| 3,949,744 | 4/1976 | Clarke | 128/214 R |
| 4,018,687 | 4/1977 | Zahour | 210/448 |
| 4,021,353 | 5/1977 | Raines et al. | 210/448 |
| 4,035,304 | 7/1977 | Watanabe | 210/317 |
| 4,066,556 | 1/1978 | Vaillancourt | 210/448 |
| 4,111,659 | 9/1978 | Bowley | 422/48 |

FOREIGN PATENT DOCUMENTS 2314753  1/1977  France ................................ 210/445

Primary Examiner—Charles N. Hart
Assistant Examiner—David R. Sadowski
Attorney, Agent, or Firm—Merchant, Gould, Smith, Edell, Welter & Schmidt

[57] ABSTRACT

A filter assembly (10) for use in the filtration of medical treatment liquids is disclosed. The filter assembly (10) includes a strip of porous filter media (12), first enclosure means (14), and a second enclosure means (16). An inlet connector (18) is connected to inlet end (20) of the filter assembly (10) and an outlet connector member (22) is connected to an outlet end of the filter assembly (10). The first and second enclosure means (14), (16) are formed of strips of flexible plastic material having longitudinal edges (30), (40) which are ultrasonically welded to the filter media (12). Dimples (36), (42) are formed in the first and second enclosure means (14), (16), respectively, and are ultrasonically welded to the filter media (12).

6 Claims, 11 Drawing Figures

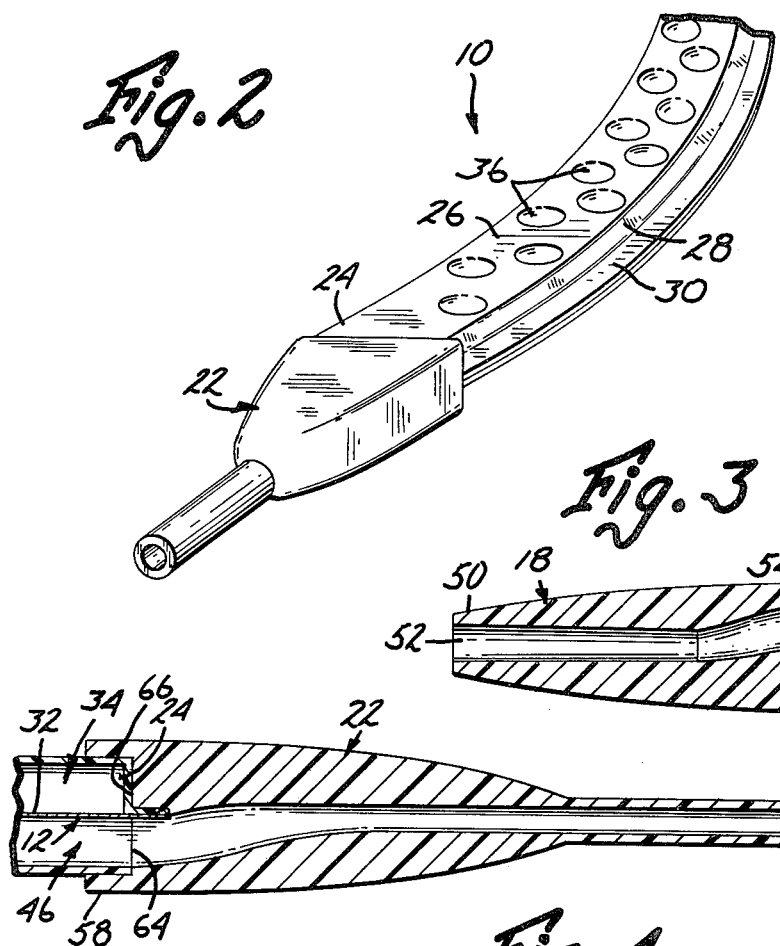

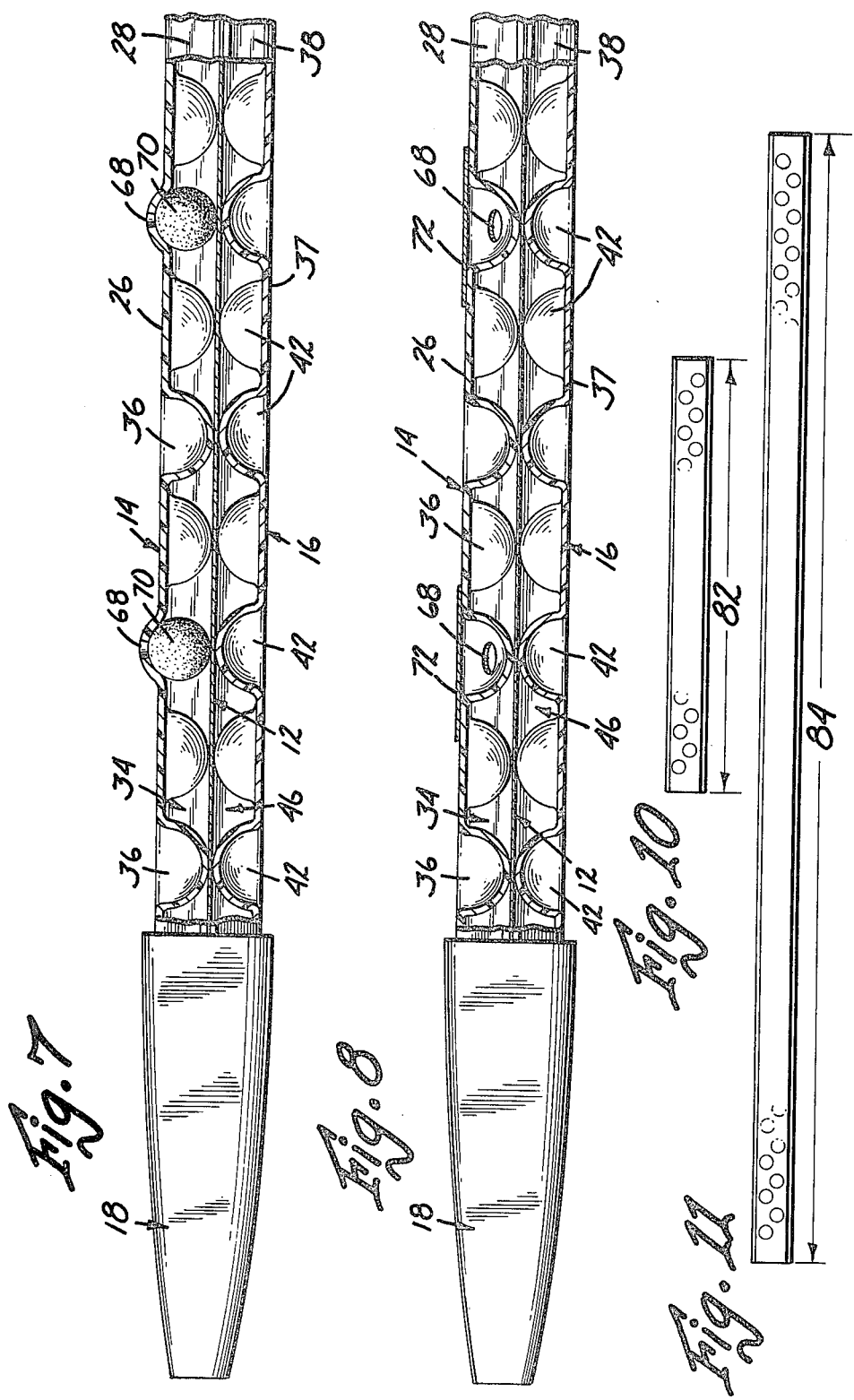

FILTER ASSEMBLY FOR USE IN THE FILTRATION OF MEDICAL TREATMENT LIQUIDS

TECHNICAL FIELD

The present invention relates to a filter assembly for use in the filtration of medical treatment liquids. More particularly, the present invention relates to a tape-type flexible filter assembly used in the filtration of IV solutions. The tape-type filter assembly can be formed in various lengths dependent upon the desired length of time which the assembly will be used.

BACKGROUND OF THE PRIOR ART

Numerous types of fluids, blood, plasma, nutritive solutions and the like, are frequently injected into a patient undergoing medical treatment. The fluids are injected either under the force of gravity or under pressure supplied by a mechanical pump. The fluids which are to be injected are, of course, produced and stored in such a manner that they should be safe for direct injection into a patient. However, micro-organisms, particles or air may enter the fluid prior to its injection into a patient. Mechanical filtration of the fluids is intended to remove such micro-organisms, particles or air. However, prior art medical filtration devices have generally been expensive and, hence, are not always used during IV treatment.

Numerous types of filters have been used to filter medical treatment solutions. A number of prior art filter assemblies, such as exemplified in U.S. Pat. No. 2,765,923 to Novak, U.S. Pat. No. 3,949,744 to Clarke, U.S. Pat. No. 4,035,304 to Watanabe, and U.S. Pat. No. 4,066,556 to Vaillancourt, utilize flexible walls to contain the filter assemblies. The filtering mechanisms disclosed in the Watanabe and Vaillancourt patents have relatively complex structures wherein a filter media is folded within a bag-type housing. The filter assembly disclosed in the Novak patent includes a pair of flexible walls secured to a central filter media along the edges of the media. However, the central walls of the Novak filter assembly are not attached to the filter media and, hence, are free to move relative thereto.

A filter assembly which utilizes a relatively rigid housing is illustrated in U.S. Pat. No. 4,021,353. Other types of filter assemblies that use rigid housings are produced by a number of manufacturers. Rigid walled filter assemblies generally have complex structures which result in high construction costs.

BRIEF SUMMARY OF THE INVENTION

The filter assembly of the present invention is designed to filter medical treatment fluids. The filter assembly includes a filter membrane comprised of a longitudinally extending strip of porous filter media having a first major surface and a second major surface. A first enclosure means is received about the first major surface of the filter media to define an inlet chamber for fluid to be filtered by the membrane. A second enclosure means is received about the second major surface of the filter media to provide an outlet chamber for fluid that has been filtered through the filter media. The first enclosure means includes a plurality of projections extending into the inlet chamber, contacting the first major surface and being attached thereto. The second enclosure means includes a plurality of projections extending into the outlet chamber, contacting the second major surface and being attached thereto. An inlet means is provided for admitting fluid to be filtered into the inlet chamber and an outlet means is provided for allowing the filtered fluid to leave the outlet chamber.

In a preferred embodiment, each enclosure means is comprised of a strip of flexible plastic material having a pair of opposed lengthwise edges. Each lengthwise edge is attached to a respective major face and the projections are comprised of dimples formed in the strips of flexible plastic material. The dimples are attached to respective surfaces of the filter media and thus serve to hold the filter assembly in shape.

Several types of vent means are disclosed. Air which may be entrapped in the liquid being filtered is vented from the filter assembly by the vent means. One type of vent means includes a plurality of vent apertures formed through the first enclosure means. The vent apertures are either covered with a hydrophobic material or a block of hydrophobic material is disposed between an aperture or group of apertures and the filter media. Another type of vent means is formed in an inlet connector member attached to the inlet end of a filter assembly.

The filter assembly preferably has a thin rectangular cross-section so that the entire filter assembly is in the form of a flexible tape. The simple configuration permits the filter assembly to be made relatively inexpensively and also permits the filter assembly to be readily made in various lengths. A short length filter assembly would be suitable for use for a short period of time, for example one to three hours, while a longer filter assembly would be suitable for use for longer periods of time, for example twenty-four hours. The cost for using the filter assemblies could thus be kept down by using shorter, less expensive filter assemblies when it is known that the filter will be required for only a short period of time.

Various advantages and features of novelty which characterize the invention are pointed out with particularity in the claims annexed hereto and forming a part hereof. However, for a better understanding of the invention, its advantages, and objects obtained by its use, reference should be had to the drawings which form a further part hereof, and to the accompanying descriptive matter, in which there is illustrated and described a preferred embodiment of the invention.

BRIEF DESCRIPTION OF THE DRAWINGS

FIG. 2 is a perspective view of a portion of a filter assembly, including an outlet end thereof, in accordance with the present invention;

FIG. 3 is a sectional view illustrating an inlet connector member;

FIG. 4 is a sectional view illustrating an outlet connector member;

FIG. 7 is a side elevational view, partially broken away, illustrating another type of vent means;

FIG. 8 is a side elevational view, partially broken away, illustrating a further type of vent means;

FIG. 9 is a side elevational view, partially broken away, illustrating another type of vent means;

FIG. 10 is a top plan view illustrating one length of a filter tape; and

FIG. 11 is a top plan view illustrating a second length of filter tape.

DETAILED DESCRIPTION OF THE INVENTION

Figure 1:
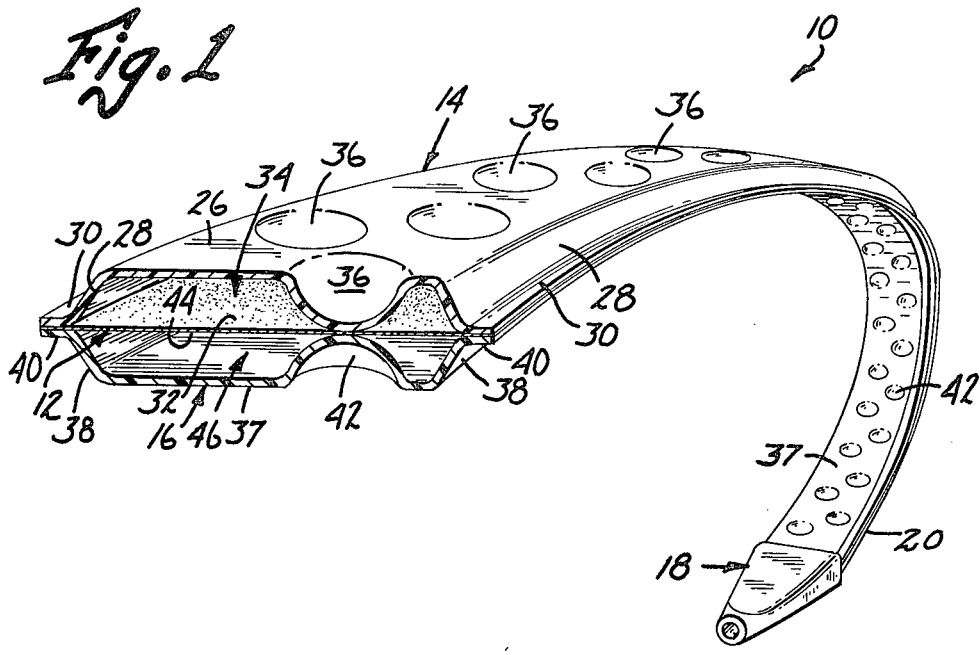
FIG. 1 is a perspective view, partially in section, illustrating a portion of a filter assembly, including an inlet end thereof, in accordance with the present invention.

Referring to the drawings in detail, wherein like numerals indicate like elements, there is shown in FIG. 1 a portion of a filter assembly designated generally as 10. The filter assembly 10 includes a strip of porous filter media 12, a first enclosure means 14, and a second enclosure means 16. An inlet connector member 18 is conencted to an inlet end 20 of filter assembly 10 and an outlet connector member 22 is connected to an outlet end 24 of the filter assembly 10.

The filter media 12 is formed from a hydrophilic membrane that has a porosity sufficiently small to filter out microorganisms and particles of the type that may be contained in fluids which are introduced intravenously to medical patients. A membrane in the range of 0.2 microns has been found suitable. Other size filter membranes, however, can be used.

The first and second enclosure means 14, 16 and made of a flexible plastic material which is of medical grade quality, and is capable of vacuum forming, the flexible plastic material also should be capable of retaining its shape after vacuum forming. The plastic material is also preferably a translucent plastic so that fluid moving through the filter assembly 10 can be observed. A frosty clear polyvinyl chloride having a thickness of approximately 0.012 inches has been found suitable.

As is best seen in FIG. 1, the filter assembly has a generally thin rectangular cross-section and the overall assembly 10 takes on the form of a tape. The first enclosure means 14 has a top, generally planar section 26. The top section 26 extends along substantially the entire lengthwise and widthwise dimension of the filter assembly 10. Extending along either side of the top section 26 along its lengthwise dimension is a pair of downwardly sloping walls 28. An edge section 30 is connected to each downwardly sloping wall 28 and forms a pair of outer lengthwise edges of the first enclosure 14. Each edge 30 is attached to a top surface 32 of the filter media 12. The preferred mode of attachment is ultrasonic welding. An inlet chamber 34 is formed between the first enclosure means 14 and the top surface 32 of the filter media 12. A plurality of projections, preferably in the form of dimples 36 formed integral with the plastic material, extend downwardly into the inlet chamber 34 from the section 26. The dimples 36 are attached to the top surface 32, preferably by ultrasonic welding. The dimples 36 are formed in a staggered or zigzag disposition along the length of the first enclosure means 14. In this manner, a tortuous path is provided through the inlet chamber 34.

The second enclosure means 16 similarly has a top section 37, downwardly extending walls 38, edges 40 and dimples 42. The edges 40 and the dimples 42 are attached to a bottom surface 44 of the filter media 12, preferably by ultrasonic welding. An outlet chamber 46 is formed between the second enclosure means 16 and the bottom surface 44 of the filter media 12. The attachment of the dimples 36 and 42 to the filter media 12 gives additional structural integrity to the filter assembly 10. When a fluid is flowing under the force of gravity through the filter assembly 10, the filter assembly 10 holds its generally rectangular shape and does not ballon outwardly due to fluid pressures. Thus, a reliable and durable filter assembly 10 is provided. The dimples 36 ad 42 are aligned in pairs. The alignment of the dimples 36, 42 simplifies the method of construction since a singe weld can be utilized to attach a pair of aligned dimples 36, 42.

The inlet connector member 18 is shown in detail in FIG. 3. The connector member 18 has a first end 48 which is connected to the inlet end 20 of the filter assembly 10 and a second end 50. The second end 50 is adapted to be connected to a fluid source by conventional connectors and tubing. A channel 52 is formed through the connector member 18 and connects the first and second ends 48, 50. The channel 52 communicates with the inlet chamber 34 through an outlet opening 54 at the first end 48. The connector member 19 has an end wall 56 at its first end 48. The end wall 56 abuts the outlet chamber 46 adjacent the inlet end 24 of the filter assembly 10 and is attached to the second enclosure means 16 and the filter media 12. The outlet chamber 46 is thus sealed at the inlet end 24. The connector member 19 thus forms an inlet means which guides fluid through the channel 52 to the inlet chamber 34.

The outlet connector member 22 is shown in detail in FIG. 4. The outlet connector member 22 has a first end 58, a second end 60 and a channel 62 formed through it. The first end 58 is connected to the first and second enclosure means 14, 16 and the filter media 17 adjacent the outlet end 24. An inlet opening 64 communicates with the channel 62 and outlet chamber 46. The second end 60 is adapted to be connected to tubing or conduits that are connected to an interavenous needle which injects the filtered fluid to a medical patient. The connector member 22 has an end wall 66 that is connected to the first enclosing means 14 and the filter media 12 to block or seal the inlet chamber 34 adjacent the outlet end 24. In this manner, fluid from the outlet chamber 46 is directed out the opening 64. Since the inlet and outlet connector members 18, 22 alternately block ends of the inlet and outlet chambers 34, 46, the fluid flowing through the filter assembly 10 is constrained to move from the inlet chamber 34, through the filter media 12 and then through the outlet chamber 46.

Air may become entrained with the fluid that is being filtered by filter assembly 10. Vent means are therefore provided in the filter assembly 10 to allow the entrained air to vent out of the filter assembly 10. Four types of vent means are illustrated in FIGS. 5, 7, 8 and 9.

Referring first to FIG. 7, the vent means includes a plurality of vent apertures 68 formed through the first enclosure means 14. The vent apertures 68 are preferably formed through the first enclosure means 14 at the area of the dimples 36. As illustrated, a single vent aperture 68 is formed through a single dimple 36, however a plurality of vent apertures 68 could be formed in a single dimple 36. The dimples 36 which have vent apertures 68 are bent outwardly away from the inlet chamber 34 instead of inwardly toward the filter media 12. A block of hydrophobic material, preferably in the form of a sphere 70, is disposed between each of the dimples 36 which contain the vent apertures 68. The spheres 70 permit the venting of air through the aperture 68 to the atmosphere, while not permitting the flow of the treatment fluid therethrough. While only two vent holes 68 and two spheres 70 are shown in FIG. 7, it should be understood that a number of vent apertures 68 and spheres 70 are disposed periodically along the entire length of the first enclosure means 14.

Referring to FIG. 8, a second type of vent means is shown. The second type of vent means also utilizes a plurality of vent apertures 68 formed periodically through the first enclosure means 14 along its entire length. In this embodiment, the vent apertures 68 are also formed through the first enclosure means 14 at a plurality of dimples 36. However, the dimples 36 through which the vent apertures 68 are formed are not bent outwardly but rather remain bent inwardly toward the filter media 12. In place of the spheres 70, pieces of hydrophobic material 72 are secured to the first enclosure means 14 above the dimples 36 which have vent apertures 68. The hydrophobic material 72 permits the flow of air out of the filter assembly 10 while keeping the treatment solution confined therein.

A third type of vent means is illustrated in FIG. 9. In the third type of vent means, only two vent apertures 68 are formed in the first enclosure means 14 (one of which is shown in FIG. 9). One vent aperture 68 is formed adjacent the inlet connector member 18 and the other vent aperture is formed through the first enclosure means 14 adjacent the outlet connector member 22. Again the vent aperture 68 is formed through a dimple 36 and the dimple 36 is bent outwardly. A block of hydrophobic material preferably in the form of a sphere 74 is interposed between the aperture 68 and the filter media 12. Since only two blocks of hydrophobic material are used, the sphere 72 is made larger than the sphere 72.

Figure 5:
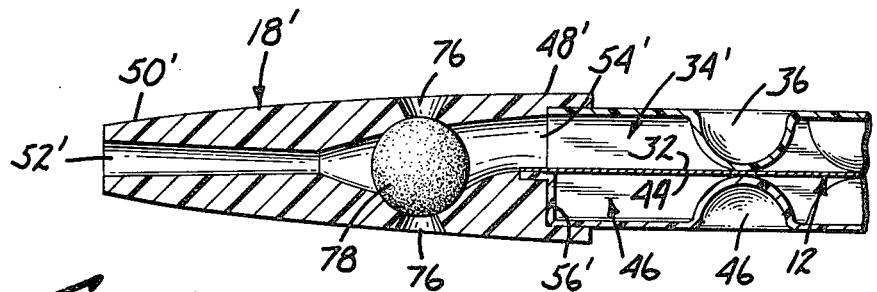
FIG. 5 is a sectional view illustrating another type of inlet connector member having a vent means.

A fourth type of vent means is illustrated in FIG. 5. In the fourth type of vent means, no vent apertures are formed through the first enclosure means 14. However, the standard connector tip 18 is replaced by a connector tip 18'. Details of the inlet connector member 18' which are similar to the inlet connector member 18 will be indicated in primed numerals. A pair of vent apertures 76 are formed through the connector member 18' and communicate with the channel 52'. A block of hydrophobic material, such as sphere 78 is disposed within the channel 52' and blocks the apertures 76. Fluid which is flowing through the channel 52' flows around the sphere 78, through the outlet opening 54' and into the inlet chamber 34. Air which may have been entrained in the fluid flowing through the channel 52' passes through the hydrophobic sphere 78 and out of the vent apertures 76.

Figure 6:
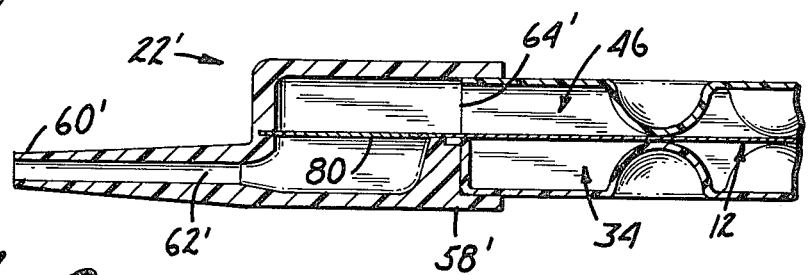
FIG. 6 is a sectional view illustrating another type of outlet connector member having a safety membrane.

An alternate outlet connector member 22' is illustrated in FIG. 6. Portions of the outlet connector member 22' which are similar to corresponding portions of outlet connector member 22 will be indicated in primed numerals. The outlet connector member 22' has a safety membrane 80 that extends across the entire cross section of the channel 62'. The safety membrane is formed of a hydrophilic material, preferably having a porosity equal to or greater than one micron. The safety membrane 80 allows the filtered fluid to pass through the channel 62' and out the second end 60' but stops the flow of any air that may still be entrained with the fluid. The safety member 80 thus serves as a safety device and can be used with any of the above-described vent means.

Since the filter assembly 10 of the present invention takes on a simple tape-like configuration, the filter assembly 10 can be readily made in various lengths. The filtering portion of a filter assembly which has a short length 82 is shown in FIG. 10. The short length 82 may, for example, be 3 inches. The filtering portion of a filter assembly which has a relatively long length 84 is illustrated in FIG. 11. The long length may for example, be 12 inches. A short length filter assembly 10 would be used to filter a solution for a relatively short period of time, for example 3 hours, while a long length filter assembly 10 would be used to filter a solution for a relatively long period of time, for example 12 or 24 hours. While only two lengths 82,84 of filtering portions of filter assembly 10 are shown in the figures, it should be understood that numerous lengths of filter assemblies 10 could be produced. For a given solution, the various lengths of filter assembly would be used for various lengths of time. Since a shorter length filter assembly would be less expensive to produce, savings to the ultimate user would result. That is, when an intravenous solution is to be injected over a short period of time, a short, rather than a long filter assembly 10 would be used. Applicant is unaware of a present filter assembly which has this capability.

Numerous characteristics and advantages of the invention have been set forth in the foregoing description, together with details of the structure and function of the invention, and the novel features thereof are pointed out in the appended claims. The disclosure, however, is illustrative only, and changes may be made in detail, especially in matters of shape, size, and arrangement of parts, within the principle of the invention, to the full extent extended by the broad general meaning of the terms in which the appended claims are expressed.

What is claimed is:

1. A filter assembly for use in the filtration of medical treatment fluids comprising:
   a filter membrane, said membrane being comprised of a longitudinally extending piece of porous filter media having a first major surface and a second major surface;
   first enclosure means received about the first major surface of said filter media to define an inlet chamber between said first enclosure means and said filter media for a liquid to be filtered by said filter media;
   second enclosure means received about the second major surface of said filter media to define an outlet chamber between said second enclosure means and said filter media for fluid filtered through said filter media;
   said first enclosure means including a first wall member of flexible material having a first enclosure major surface extending over said first major surface, said flexible material being impermeable to liquid and gas;
   said second enclosure means including a second wall member of flexible material having a second enclosing major surface extending over said second major surface, said last-mentioned flexible material being impermeable to liquid and gas, each wall member comprising a strip of flexible plastic material having opposed lengthwise edges, each lengthwise edge of said strip comprising said first enclosure means being attached to the first major surface of said filter media and each lengthwise edge of said strip comprising said second enclosure means being attached to the second major surface of said filter media;
   means for preventing the ballooning of the flexible material of said first and second wall member away from said filter membrane, said ballooning preventing means including a first plurality of projections and a second plurality of projections, said first plurality of projections being formed in the first enclosing major surface and extending into said inlet chamber, contacting said first major surface of said filter membrane and being fixedly attached thereto, said second plurality of projections being formed in the second enclosing major surface and extending into said outlet chamber, contacting said second major surface of said filter membrane and being fixedly attached thereto, said projections comprising dimples formed in said flexible plastic material;

inlet means for admitting fluid to be filtered into said inlet chamber;

outlet means for allowing filtered fluid to leave said outlet chamber;

means for venting from said filter assembly air entrained in a liquid being filtered by said filter assembly, said vent means including a plurality of apertures through the first enclosure means and discrete blocks of hydrophobic material disposed between said apertures and said filter media, said apertures being formed through a plurality of the dimples of said first enclosure means, each of the dimples having an aperture through it being bent outwardly away from said filter media, and one of said discrete blocks of hydrophobic material being disposed between each of said apertured dimples and said filter media, each of said blocks of hydrophobic material being in the shape of a sphere.

2. A filter assembly in accordance with claim 1 wherein each dimple formed in the material of said first enclosure means is aligned with one of the dimples formed in the material of said second enclosure means whereby said filter media is supported between a plurality of aligned pairs of dimples.

3. A filter assembly for use in the filtration of medical treatment fluids comprising:

a filter membrane, said membrane being comprised of a longitudinally extending piece of porous filter media having a first major surface and a second major surface;

first enclosure means received about the first major surface of said filter media to define an inlet chamber between said first enclosure means and said filter media for a liquid to be filtered by said filter media;

second enclosure means received about the second major surface of said filter media to define an outlet chamber between said second enclosure means and said filter media for fluid filtered through said filter media;

said first enclosure means including a first wall member of flexible material having a first enclosing major surface extending over said first major surface, said flexible material being impermeable to liquid and gas;

said second enclosure means including a second wall member of flexible material having a second enclosing major surface extending over said second major surface, said last-mentioned flexible material being impermeable to liquid and gas;

means for preventing the ballooning of the flexible material of said first and second wall member away from said filter membrane, said ballooning preventing means including a first plurality of projections and a second plurality of projections, said first plurality of projections being formed in the first enclosing major surface and extending into said inlet chamber, contacting said first major surface of said filter membrane and being fixedly attached thereto, said second plurality of projections being formed in the second enclosing major surface and extending into said outlet chamber, contacting said second major surface of said filter membrane and being fixedly attached thereto;

inlet means for admitting fluid to be filtered into said inlet chamber, said inlet means including a first connector member having a first end connected to an inlet end of said filter assembly and a second end adapted to be attached to a fluid source, said first connector member having a channel through it connecting said first and second ends and said first end having a port for providing communication between said channel and said inlet chamber, and first sealing means for sealing an end of said outlet chamber at the inlet end of said filter assembly;

outlet means for allowing filtered fluid to leave said outlet chamber;

means for venting from said filter assembly air entrained in a liquid being filtered by said filtering assembly, said venting means including a pair of vent apertures formed through said first connector member, aligned with one another, and communicating with said channel at a location between said first and second ends of said first connector member, and a block of hydrophobic material in the form of a sphere disposed in said channel and blocking both of said vent apertures.

4. A filter assembly in accordance with claim 3 wherein said projections are comprised of dimples formed in said flexible plastic material.

5. A filter assembly for use in the filtration of medical treatment fluids comprising:

a filter membrane, said membrane being comprised of a longitudinally extending strip of porous filter media having a first major surface and a second major surface;

first enclosure means received about the first major surface of said filter media to define an inlet chamber between said first enclosure means and said filter media, said first enclosure means being comprised of a first strip of flexible plastic material which is impermeable to liquid and gas and which has opposed lengthwise edges ultrasonically welded to the first major surface of said filter media;

second enclosure means received about the second major surface of said filter media to define an inlet chamber between said second enclosure means and said filter media, said second enclosure means being comprised of a second strip of flexible plastic material which is impermeable to gas and liquid and which has opposed lengthwise edges ultrasonically welded to the second major face of said filter media;

means for preventing the ballooning of said first and second wall members away from said filter media, said ballooning preventing means including a first and a second plurality of dimples attached to said filter media;

said plurality of first dimples being formed in the first strip of flexible plastic material along its length and between its opposed lengthwise edges, said first dimples being bent inwardly into said inlet chamber and being ultrasonically welded to the first major surface of said filter media;

said plurality of second dimples formed in the first strip of flexible plastic material along its length and between its lengthwise edges, said second dimples being bent into said outlet chamber and being ultrasonically welded to the second major surface of said filter media;

inlet means for admitting fluid to be filtered into said inlet chamber;

outlet means for allowing filtered fluid to leave said outlet chamber;

vent means for venting from said filter assembly air entrained in a liquid being filtered by said filter assembly; and said vent means including apertures formed through a plurality of dimples of said first enclosure means, each of the dimples having an aperture through it being bent outwardly away from said filter media, and a sphere of hydrophobic material being disposed between each of said apertured dimples and said filter media.

6. A filter assembly in accordance with claim 5 wherein each dimple formed in the strip of said first enclosure means is aligned with one of the dimples formed in the strip of said second enclosure means whereby said filter media is supported between a plurality of aligned pairs of dimples.

* * * * *